(12) United States Patent
Pigg et al.

(10) Patent No.: US 8,505,162 B2
(45) Date of Patent: Aug. 13, 2013

(54) ADHERENCE-AIDED THERAPEUTIC HORSE HOOF PACKING

(75) Inventors: Frederick Pigg, Azle, TX (US); Frank Rovelli, Oxnard, CA (US); Paul Porteous, Oxnard, CA (US)

(73) Assignee: Vettec, Inc., Oxnard, CA (US)

( * ) Notice: Subject to any disclaimer, the term of this patent is extended or adjusted under 35 U.S.C. 154(b) by 1085 days.

(21) Appl. No.: 11/720,334

(22) PCT Filed: Oct. 10, 2006

(86) PCT No.: PCT/US2006/039616
§ 371 (c)(1),
(2), (4) Date: May 28, 2007

(87) PCT Pub. No.: WO2008/033148
PCT Pub. Date: Mar. 20, 2008

(65) Prior Publication Data
US 2009/0173288 A1    Jul. 9, 2009

(51) Int. Cl.
*A01N 59/16*    (2006.01)

(52) U.S. Cl.
USPC ............... 16/29; 16/27; 424/404; 424/617; 424/630

(58) Field of Classification Search
USPC ........ 16/27, 29; 424/404, 617, 630; 524/198
See application file for complete search history.

(56) References Cited

U.S. PATENT DOCUMENTS

| | | | |
|---|---|---|---|
| 3,285,346 A | 11/1966 | Jenny et al. | |
| 3,630,289 A | 12/1971 | Norberg | |
| 3,682,179 A | 8/1972 | Firth et al. | |
| 3,899,807 A | 8/1975 | Sovish et al. | |
| 4,182,340 A | 1/1980 | Spencer | |
| 4,237,981 A | 12/1980 | Stubbe | |
| 4,565,250 A | 1/1986 | Vasko | |
| 4,691,782 A | 9/1987 | Stine | |
| 4,765,411 A | 8/1988 | Tennant | |
| 4,869,400 A | 9/1989 | Jacobs | |
| 4,888,225 A | 12/1989 | Sandvig et al. | |
| 4,896,727 A | 1/1990 | Busser | |
| 4,917,192 A | 4/1990 | Monticello | |
| 4,982,797 A | 1/1991 | Monticello | |
| 5,069,289 A | 12/1991 | Schaffer | |
| 5,189,117 A | 2/1993 | Hefner, Jr. | |
| 5,199,498 A | 4/1993 | Knudsen | |
| 5,213,163 A | 5/1993 | Schaffer | |
| 5,222,561 A | 6/1993 | Fisher et al. | |
| 5,330,008 A | 7/1994 | Sigafoos et al. | |
| 5,407,620 A | 4/1995 | Burchette et al. | |
| 5,451,629 A | 9/1995 | Jacobs | |
| 5,505,264 A | 4/1996 | Morris et al. | |
| 5,681,350 A | 10/1997 | Stovall | |
| 5,698,623 A | 12/1997 | Jacobs | |
| 5,699,861 A | 12/1997 | Sigafoos | |
| 5,706,898 A | 1/1998 | Beadle | |
| 5,780,064 A * | 7/1998 | Meisters et al. | 424/616 |
| 5,798,409 A | 8/1998 | Ho | |
| 6,009,952 A | 1/2000 | Porteous et al. | |
| 6,021,851 A | 2/2000 | Jacobs | |
| 6,196,326 B1 | 3/2001 | Jacobs | |
| 6,412,566 B1 * | 7/2002 | Rovelli et al. | 168/4 |
| 6,497,292 B2 | 12/2002 | Rovelli | |
| 6,505,686 B2 | 1/2003 | Rovelli | |
| 2005/0121205 A1 * | 6/2005 | Kelly | 168/4 |

FOREIGN PATENT DOCUMENTS

| | | |
|---|---|---|
| DE | 37591 | 4/1886 |
| DE | 39669 | 10/1886 |
| DE | 132785 | 7/1902 |
| DE | 272466 | 12/1911 |
| DE | 2630444 | 1/1978 |
| DE | 3841925 | 6/1989 |
| EP | 308309 | 3/1989 |
| EP | 1076074 | 2/2001 |
| FR | 673451 | 1/1930 |
| FR | 2641942 | 7/1990 |
| GB | 1125 | 0/1905 |
| GB | 1290 | 0/1904 |
| GB | 8323 | 0/1890 |
| GB | 18964 | 0/1900 |
| GB | 1405211 | 9/1975 |
| WO | WO9406285 A1 | 3/1994 |

\* cited by examiner

*Primary Examiner* — Ali Soroush
(74) *Attorney, Agent, or Firm* — Koppel, Patrick, Heybl & Philpott; Michael J. Ram (57) ABSTRACT

Horse hoof protection against thrush conditions is obtained by depositing onto the horse hoof bottom wall a synthetic organic resin such as a urethane resin through which a medicament that does not block cure of the resin has been, distributed for continuing hoof wall contact. The resin is suitably free flowing into place, conforms to the contours of the hoof bottom wall, and adheres to the wall when cured. The protection by the resin is resilient and softer than the hoof wall and acts to cushion the hoof against shock.

59 Claims, 1 Drawing Sheet

ADHERENCE-AIDED THERAPEUTIC HORSE HOOF PACKING

BACKGROUND OF THE INVENTION

1. Technical Field

This invention relates to methods and compositions for the anti-microbial treatment of animals through the persistent application of treating medicaments in an adherent resinous matrix, and, more particularly, to relief of thrush conditions in hoofs of horses and similar conditions in other affected animals. The invention relates to improvements in the delivery of therapeutic medicaments to hoofs through provision of a system that not only carries the therapeutic agents to the hoof but maintains the therapeutic dose on the affected area such as the hoof bottom wall, for as long as desired, at a near constant dosage by adhering to the wall the therapeutic agent in treatment proximity. Methods, compositions, and products of the invention include therapeutic agent modified and adhesion improved horse hoof packing compositions, horse hoof treatment of thrush conditions with such packing, and treated hooves.

2. Related Art

In typical horse care, webs or pads of leather, plastic or rubber are attached to the hoof edge walls, and sized to extend across the hoof sole and cover the frog portion of the hoof, e.g. inserted between the horseshoe and the hoof edge walls to protect the sensitive areas of the hoof. Moisture or debris sometimes work their way into the hoof open volume defined broadly by the hoof bottom wall (comprising the hoof sole and frog) and the surrounding hoof portion, causing discomfort in or harm to the animal. Efforts to fill the volume against debris incursions have involved adding packing including resins to the sole and covering with the web or pad. Until the introduction of the EQUI-PAK® hoof packing products of Vettec, Inc. these expedients did not prove successful because of difficulties in handling other resins, excessive viscosity that militated against readily filling into the horse hoof volume, persistent resin tackiness, lack of fill of all interstices or voids within the volume, leaving places for moisture accumulation, undue final hardness of the resin, and, with particular pertinence here, other resins did not adhere to the web used to cover the hoof frog, leaving space between the resin mass and the web or pad that allowed detrimental incursions of debris. The EQUI-PAK® hoof packing products although initially free flowing for easy filling of interstices, set fast, in seconds, had a range of flexibilities, were non-porous, adhered to the hoof wall, were clear, and could be applied with or without a protective pad.

Thrush is among the most common infections in equine hooves. It is generally described as a microbial infection of the frog which may result from confinement in filthy conditions. Thrush is a microbial "soup" composed of a multitude of bacteria, algae, mold, yeasts, and fungi which colonize the frog and slowly degrade it and surrounding tissues. While the infection is typically not life threatening it can cause inflammation of the affected hoof and may result in lameness. The physical manifestation of the infection is a gooey black discharge from the hoof coupled with the noxious odor of decaying organic matter.

In many cases the presence of a thrush condition can be eliminated by improving the living conditions of the horse. Clean, dry, urine- and manure-free living quarters, as well as time spent in open pasture, will typically eliminate the condition. At times, however, weather or other circumstances restrict availability of these ideal living conditions and thrush becomes an issue. In such cases treatment with a commercial remedy is indicated. Many medical and art-based remedies are known for-thrush, including sources of copper ions, such as copper salts. Copper salts such as copper sulfate, and copper compounds in general, have long been used as anti-microbial treatments, including algaecides and fungicides.

SUMMARY OF THE INVENTION

In the field users have put EQUI-PAK® and other hoof packing products on top of anti-thrush medications, but this has led to a loss of some desired properties of the EQUI-PAK® hoof packing products as the presence of anti-microbials can reduce the important (to excluding moisture) adhesion property of these hoof packing products, creating new places for moisture and thus thrush to flourish despite simultaneously trying to eliminate the thrush condition.

It is an object of the invention accordingly to provide methods, compositions and products for improving the health of hoofed animals particularly horses. It is a further object to provide a method of treating horse hoof thrush conditions with medicaments held to the affected area by a material that bodily incorporates the medicament. Another object is to deplete the material of moisture with a hygroscopic adjuvant that also functions as a medicament. A further object is to deposit a medicament carrying fluid resin into the affected area from one container or from dual cartridges containing separate, reactive precursor components of the hoof packing material, and the medicament as well. Another object is to provide a thrush treated horse hoof having a hoof packing material therein that is intimately mixed with particulate medicament typically a sulfate salt that migrates, seeps, blooms or otherwise rises to the interface of the hoof bottom wall and the hoof packing to treat the thrush without inhibiting adhesion between the hoof packing and the hoof bottom wall. A still further object is provision of a thrush treatment and product using a synthetic organic resin matrix and distributed therein a small but therapeutically effective anti-thrush medicament such as a hydrated copper sulfate at about 0.5 to about 5% by weight, preferably 1-3% by weight, the resin matrix, typically an acrylic, epoxy, polysulfide, or silicone resin, and preferably a urethane resin, being conformed to the hoof bottom wall in operating proximity to the thrush condition. Yet another object is provision of a thrush treating system having separately packaged resin precursors to be mixed in reactive proportions, and a therapeutic agent that in amount and nature does not, i.e. is ineffective to block reaction of the precursors or the bonding of the resin product to the hoof bottom wall to achieve a covering thereof, the therapeutic agent being precursor-dispersed in premixed relation. More broadly, the invention objects include providing a medicated hoof treating including packing methods and compositions that flow easily and readily into the hoof volume onto the hoof bottom wall and the interstices thereof yet sets up nearly immediately to a firm, somewhat resilient mass that adheres to the hoof volume walls against loss of the mass or incursions of debris.

These and other objects of the invention to become apparent hereinafter are realized in a method of treating an animal hoof having a thrush condition, including cleaning the hoof bottom wall of debris, depositing onto the hoof bottom wall an adherent, rapidly curing synthetic organic resin composition comprising the resin and dispersed throughout for continuing hoof bottom wall contact a small but effective amount of an anti-microbial comprising a metal ion donor that does not block said curing of the composition, maintaining the resin composition at a viscosity to flow freely to conform to the contours of the hoof bottom wall, thereafter curing the resin composition to a solid in situ on the hoof bottom wall, and removing the cured resin solid after an effective period of treatment.

The invention further includes in this and like embodiments, moisture incursion-proof sealing the thrush condition with the cured resin composition solid on the hoof bottom wall during the period of treatment, selecting a copper ion donor as the anti-microbial, selecting a hydrated form of copper sulfate as the copper ion donor, and selecting a urethane resin as the composition resin.

In a further embodiment the invention includes the method of treating a horse's hoof having a thrush condition, including cleaning the hoof bottom wall of debris, depositing onto said hoof bottom wall an adherent, rapidly curing synthetic organic resin composition comprising the resin and dispersed throughout for continuing hoof bottom wall contact a small but effective amount of an antimicrobial comprising a metal ion donor that does not block curing of the composition, maintaining the resin composition at a viscosity to flow freely to conform to the contours of the hoof bottom wall, and thereafter curing the resin composition to a solid in situ on the hoof bottom wall, and removing the cured resin solid after an effective period of treatment.

In this and like embodiments, typically, the invention further includes moisture incursion-proof sealing the thrush condition with the cured resin composition solid on the hoof bottom wall during the period of treatment, selecting a copper ion donor as the anti-microbial, selecting a hydrated form of copper sulfate as the copper ion donor, and selecting a urethane resin as the composition resin.

In a further embodiment, the invention provides a method of treating a horse hoof for a thrush, including cleaning the hoof bottom wall of debris, depositing onto the hoof bottom wall an adherent, rapidly curing synthetic organic resin composition comprising the resin and dispersed throughout for wall contact a small but effective amount of a thrush medicament comprising a copper salt that does not block the curing of the composition, the resin composition having a viscosity to flow freely to conform to the contours of the hoof bottom wall before curing, curing the resin to a solid in situ on the hoof bottom wall, and removing the cured resin after an effective period of treatment.

In this and like embodiments, typically, the method also includes selecting copper sulfate as the medicament, selecting a hydrated form of copper sulfate as the medicament, selecting copper sulfate pentahydrate as the medicament, dispersing from about 0.5 to about 5% by weight of the copper salt medicament in the resin composition, dispersing as the small but effective amount of medicament about 1-3% by weight of the copper salt, selecting a two part resin as the resin and incorporating the medicament, e.g. copper sulfate pentahydrate, into one part of the resin for dispersal in the resin composition upon mixing of the two resin parts.

In a further embodiment, the invention provides a method of treating a horse's hoof for thrush, including cleaning the hoof bottom wall of debris, depositing onto the hoof bottom wall an adherent, rapidly curing urethane resin composition comprising Part A and Part B urethane resin precursors and dispersed in at least one Part for wall contact a small but effective amount of a thrush medicament comprising a copper salt that does not block the curing of the resin composition upon mixing of the precursors, the resin composition having a viscosity to flow freely to conform to the contours of the. hoof bottom wall before curing, curing the resin to a solid in situ on the hoof bottom wall with said medicament in wall contact, and removing the cured resin and medicament after an effective period of treatment.

In this and like embodiments, typically, the invention further includes selecting copper sulfate as the medicament, selecting a hydrated form of copper sulfate as the medicament, selecting copper sulfate pentahydrate as the medicament, dispersing as said small, but effective amount from about 0.5 to about 5%, or from about 1 to about 3%, by weight of the copper salt medicament in the resin composition, incorporating the copper medicament, e.g. copper sulfate pentahydrate, into Part B of the resin for dispersal in the resin composition upon mixing of the resin Parts A and B, combining the resin Parts A and B from separate cartridges thereof in a single mix tip and depositing the resulting resin composition onto the hoof bottom wall, defining an at least partially closed volume over the hoof bottom wall, and depositing said resin composition into said volume against said hoof bottom wall, self-adhering the urethane resin composition to the hoof bottom wall in moisture excluding relation, and/or maintaining a hygroscopic amount of the copper salt in the urethane resin composition against moisture inhibition of cure of the in hoof composition.

In a further embodiment, the invention provides a method of treating a horse's hoof for thrush with a normally moisture reactive urethane resin composition, depositing onto the bottom wall of the hoof a wall-adherent, rapidly curing urethane resin composition comprising two-part urethane resin precursors and dispersed in at least one part for hoof bottom wall contact a small but effective amount of an adjuvant comprising a thrush medicament that is hygroscopic against moisture reaction of the urethane resin composition and that does not block the curing of the resin composition upon mixing of the precursors, the resin composition having a viscosity to flow freely to conform to the contours of the hoof bottom wall before curing, and curing the resin to a solid in situ on the hoof bottom wall.

In this and like embodiments, typically, the invention method further includes selecting copper sulfate as the adjuvant.

In a further aspect the invention includes a method of treating for thrush a horse's hoof having a hoof bottom wall, including combining from a pair of cartridges into a static mixer separate reactive urethane resin precursors, maintaining a thrush medicament in an effective amount in one of the precursors during the combining of precursors, forming a rapidly curing urethane resin from said precursors in an amount suitable for covering the hoof bottom wall, conforming the urethane resin to the contours of the hoof bottom wall, curing the urethane resin in situ, and later removing the urethane resin and medicament.

In a still further aspect, the invention includes providing a thrush treated horse's hoof comprising a hoof having a hoof bottom wall and a solid synthetic organic resin composition containing distributed therethrough for continuing wall contact a small but therapeutically effective amount of an anti-thrush medicament conformed with and adhered to the hoof bottom wall.

In this and like embodiments, the invention also includes the medicament comprising copper sulfate, e.g. a hydrated form of copper sulfate, such as copper (cupric) sulfate pentahydrate, the resin composition comprising from 0.5 to 5% by weight of the medicament, the resin composition being a urethane resin composition, the medicament comprising a hydrated copper sulfate and being about 1-3% by weight of the composition.

The invention further includes an embodiment comprising a thrush treatment for application to horse's hoof having a hoof bottom wall, the treatment comprising a synthetic organic resin composition containing distributed therethrough a small but therapeutically effective amount of an anti-thrush medicament and conformed with and adhered to the hoof bottom wall.

In this and like embodiments, typically, the medicament comprises copper sulfate and is present from about 0.5 to 5% by weight within the treatment composition, the copper sulfate comprises a hydrated form of copper sulfate, such as copper sulfate pentahydrate present in an amount of about 1-3% by weight within the treatment, and the synthetic organic resin composition is a urethane resin composition.

A further invention embodiment includes a thrush treating product comprising separate precursors reactive upon mixing to a synthetic organic resin, one of the precursors comprising a small but effective amount of an anti-thrush medicament, and a mixing structure for uniformly mixing the precursors and the medicament adjacent a horse hoof wall at a viscosity adapted to substantially conform to and fill the spaces of a bottom wall surface in adhering relation.

In this and like embodiments, typically the anti-thrush medicament comprises copper sulfate, such as a hydrated form of copper sulfate, e. g. copper sulfate pentahydrate, that comprises from 0.5 to 5% by weight of the separate reactive precursors taken together, particularly a copper sulfate and is present from about 0.5 to 5% by weight, such as copper sulfate pentahydrate present an amount of about 1-3% by weight.

In another embodiment, the invention provides a thrush treating system having separately packaged resin precursors to be mixed in reactive proportions, and a small but therapeutically effective amount of an anti-thrush medicament that is ineffective to block reaction of the precursors, the medicament being precursor-dispersed in premixed relation.

In this and like embodiments, typically, the anti-thrush medicament comprises copper sulfate, such as a hydrated form of copper sulfate, e.g. copper sulfate pentahydrate, the medicament comprises from 0.5 to 5% by weight of the separate reactive components taken together, and particularly copper sulfate pentahydrate present an amount of about 1-3% by weight.

BRIEF DESCRIPTION OF THE DRAWINGS

The invention will be further described in conjunction with the accompanying drawings in which the single FIGURE is a schematic elevational view of the invention application of a medicament modified resin to a horse hoof shown vertically disposed rather than generally horizontal as is more typical.

DETAILED DESCRIPTION

The invention provides a simple system involving a single product that combining antimicrobial properties, e.g. of an intimately distributed copper sulfate with the hoof protective properties of an accepted hoof bottom wall covering such as a hoof packing composition surprisingly accomplishes both functions given the fragile chemistry of the resin hoof packing materials that finds added salts inimical to reactivity and final properties, and the previously experienced loss of adhesion when sulfate salts are present at the interface of the resin packing and the hoof bottom wall.

The invention compositions include a urethane resin formula which contains finely divided copper sulfate, e.g. less than about 100 U.S. Mesh that will suspend in the urethane system, e.g. with about 0.5-2% by weight of fumed silica as an aid as needed. The single step application of medicament containing hoof packing material to a cleaned, but thrush infected hoof is revolutionary in the treatment of thrush. The minimal, excreted, bloomed, or otherwise present-from-within copper sulfate layer at the hoof/urethane boundary in the invention compositions is insufficient to block adhesion but sufficient to inhibit further microbial growth, thereby correcting the thrush condition. Further, bonding of the hoof packing to the hoof bottom wall effectively blocks further ingress of fluids, providing a further thrush control mechanism through limiting more moisture incursions; thrush outbreaks thus can be controlled even under less than ideal conditions with the invention methods and products.

Given the former realization that mere application of a urethane hoof packing onto a previously deposited copper sulfate powder treated hoof was detrimental to adhesion, it is further surprising that the invention compositions are improved in adhesion to hoof tissues even over standard, nonmedicament-containing urethane compositions. While not wishing to be bound to any particular theory in may be that because copper sulfates are known to be used to remove trace amounts of water from organic chemical systems, they may be functioning in the invention urethane resin systems to remove moisture present. If so, it is known urethane chemical theory that removal of water from the adherend-urethane adhesive interface will improve adhesion. The invention urethane systems described more particularly in the patents cited below that are hereby incorporated herein as though fully set forth function best when chemically dry (free from trace amounts of water), i.e. remain stable and perform at their optimum. Thus it may be that the inclusion of a hygroscopic salt, e.g. a copper sulfate salt within the urethane resins reacts with and consumes any water chance-retained in the unreacted precursor reagents of the urethane system where the salt may be premixed, further reacts with and consumes any remaining water upon reaction of the two components to the urethane resin, and finally further reacts with and consumes water present on the hoof at the point of application, Each individual water scavenging step serves to improve product performance and adhesion to the hoof. Thus, the present invention in its several aspects combines the unique features of a two-component urethane system with antimicrobial properties from e.g. a copper sulfate without detracting from either. The bodily inclusion of copper sulfate medicament further serves to remove trace amounts of water from the two component urethane system and from the substrate upon which the system is applied thereby improving product performance, adhesion, and protection of the hoof, while delivering an effective antimicrobial agent directly to the point of need.

By way of background, horse hoofs are conventionally shod by nailing a horseshoe to the horny wall forming the outer portion of the hoof. Within the horny wall are the sole of the hoof and the sensitive frog portion of the hoof, generally referred to herein jointly and severally as the hoof bottom wall. These portions of the hoof are not protected from damage from contact with moisture or other forms of debris and harmful objects. It is a common practice to add a web across the hoof sole, usually supported by the horseshoe or horseshoe nails to protect the sole of the hoof. Debris can enter the open volume defined by the hoof bottom wall, even under the web unless the volume is filled with a suitable material. Suitable materials will fill all spaces in the volume and prevent voids and interstices from occurring. In the past, foam resins have been employed, but they do not hold up against the stresses imposed in use and allow incursions of debris, moisture and contamination. Other materials are stiff and difficult to work with and like the foam systems do not adhere to the hoof bottom wall and thus allow, especially after wearing for a time, the incursion of debris which is uncomfortable and even harmful to the horse. The present invention resins provide a solid, noncellular, void-free resin covering body, suitably adherent to the hoof bottom wall against incursive attacks from debris and moisture even after a time of use. The preferred resins herein are depositable e.g. are injectable using dual cartridge dispensers which direct reactive components of low viscosity through a static mixer onto the hoof bottom wall where their initially low viscosity enables flow throughout the volume and into the nooks, crannies, interstices and voids of the volume and occurring on the hoof walls. The resin then sets up and adheres to the walls, void-free and more resilient than the surrounding hoof to cushion the steps of the horse while protecting from debris incursions.

Figure 1:
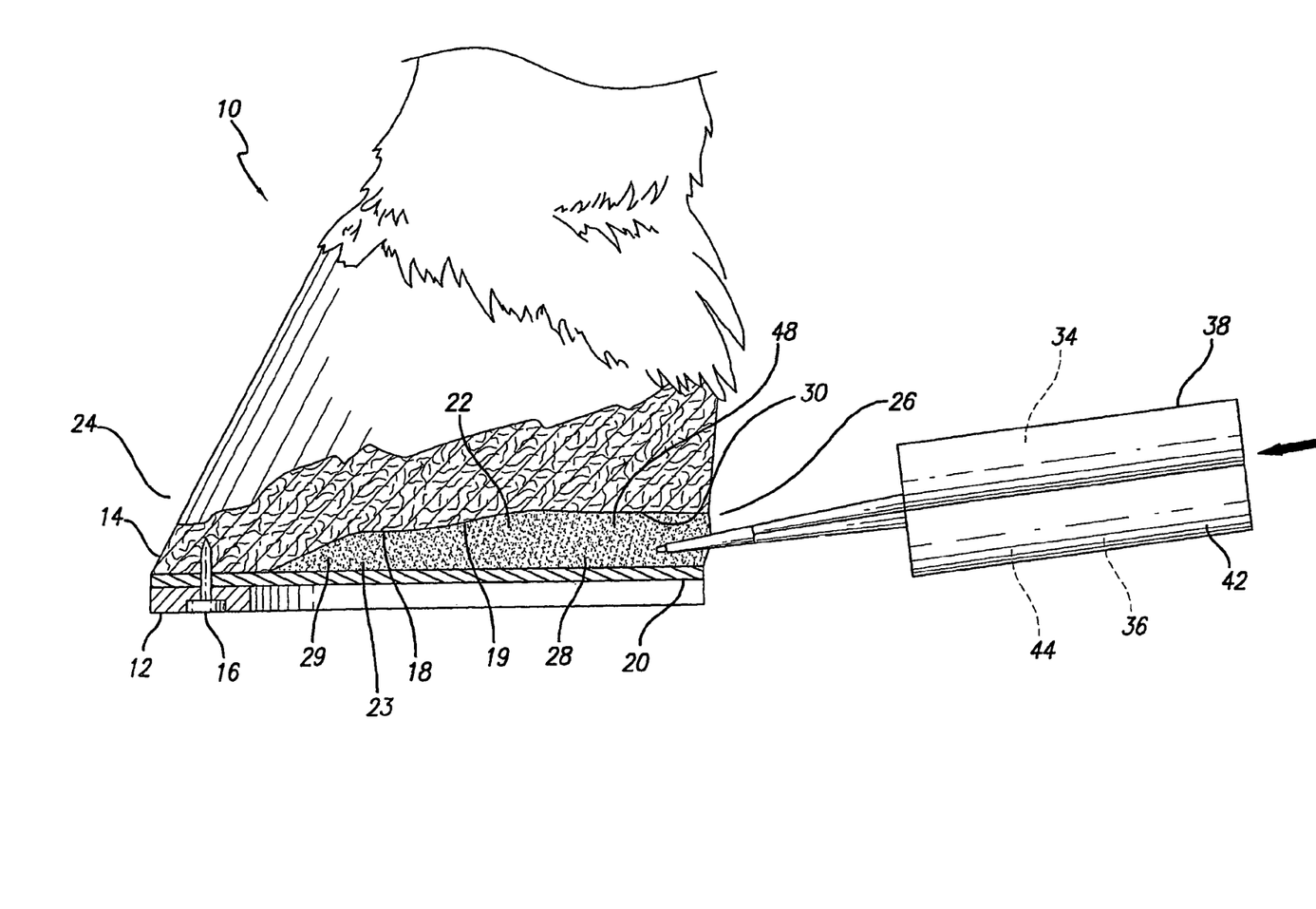

With reference to the single FIGURE, and initially with reference to the resinous hoof-packing material that will be modified with the noted medicaments, the hoof 10 is shod with a shoe 12 fixed to the hoof wall 14 by nails 16. A leather, synthetic organic resin plastic, or rubber material web 20 is stretched across the hoof sole portion 18, and anchored there by the nails 16 and horseshoe 12. The web 20 can be also affixed by any other suitable means such as adhesive, clamps, and the like. The use of the web is not necessary with the present resin masses owing to their rapid increase in viscosity within the hoof volume 22 and their final adhesion to the hoof bottom wall 19 sole and frog portions, 18, 30.

The hoof open volume 22 is defined by the hoof bottom wall 19, comprising the hoof sole portion 18 and the hoof frog portion 30, has a mouth 23 which is closed by the web 20 extending laterally between the left and right portions 24, 26 of the hoof horny wall 14. The volume 22 is filled with an injectable, e.g. liquid resin, forming a mass 28 having the compositions described herein. Because of rapid cure of the resin, e.g. in from less than 25 seconds to less than about 2 minutes, there is no need to support the resin in place until cure as with a web 20, particularly with the faster curing resins, The terms hydraulically filled and hydraulically full herein refer to the filling with the liquid resin mass 28 of substantially all the voids, crevices and interstices of the hoof sole portion 18 including areas surrounding and covering the frog portion 30 of the hoof, and to filling the volume 22 from the hoof sole 18 to the web 20 so that incursions of debris including moisture into the volume 22 are blocked.

The resin used to form the mass 29 is desirably a highly fluid liquid which can be and preferably is injected into the volume 22 to spread throughout the volume, to contact all surfaces therein, and to adhere to such surfaces in a void-eliminating manner. Resin precursors, such as those taught in the patents cited below, e.g. for a Side A isocyanate containing precursor 34 and a Side B polyol containing resin precursor 36 that is typically used to carry the medicament to produce a urethane resin, are separately packaged in piston and cylinder dual cartridges 38, 42 of dispenser 46 with the medicament 44 added to one of the precursors, suitably the Side B precursor, and further suitably in finely divided powder or slurry form. The two precursors 34, 36 are expressed from their respective cartridges 38, 42 with hand pressure or with a caulking-type gun or other means and upon such expression are intensively mixed in cartridge-attached static mix tip 43 and injected into volume 22 to be deposited onto the hoof bottom wall 19 as shown in FIG. 1.

The resultant urethane resin mass 28 is solid and being free of foam-formers will be free of voids and pockets of air or gas when cured, unlike foam systems which deliberately create voids. The resin mass 28 cures in place, i.e. in situ. Viscosities of the fluid form of the mass 28 are selected such that the incorporation of the mass into the volume 22 is quickly accomplished, in a matter of 5 to 20 seconds typically and usually less than a few minutes. Incorporation by injection rather than by hand packing as has been common with non-fluid volume fillers enables rapid distribution of the resin mass 28 through the volume 22 and the infilling of voids and interstices of the hoof bottom wall surfaces. Viscosities of less than about 25,000 and preferably less than 2500 centipoises may be used, with viscosities as low as that of water being useful. The resin can be any of the various known thermoplastic resins or thermosetting resins such as listed above meeting the invention criteria of low viscosity upon incorporation such as by injection under the web, and rapid gelling or cure to a substantially solid viscosity, e.g. 100,000 centipoises. A rapidly high viscosity gives the resin mass 28 the ability to not flow from the volume 22. This increased viscosity preferably happens in 10 to 20 seconds or less than 25 seconds, but other times, up to 2 minutes or more where conditions permit, and where the foregoing handling criterion is met can be used. Resin compositions are usefully packaged in dual cartridge packages from which they may be discharged through a static mixer tip to combine into a reactive mixture which is injectable into the volume 22. For rapid cure to a sufficiently gelled state, the amount of catalyst should be selected in concert with desired cure time, e.g. 5% by weight of a urethane reaction catalyst for a 20 second cure to the adequately gelled state, with final cure occurring over the next day or so.

While resins, such as the preferred urethane resins herein may be initially tacky, this tackiness is lost upon fully curing. The preferred application method of incorporation by injection mentioned above makes tackiness or not unimportant since the resins can be injected directly under the previously applied web, if used, and no hand or spatula contact is required, even where the web is not used.

A useful resin herein is a urethane resin prepared from one or more isocyanates, catalysts, and various polyols, such as disclosed in U.S. Pat. Nos. 4,869,400; 6,009,952; 6,131,665 and 6,412,566, the disclosures of which are hereby incorporated herein in their entirety. Desirably the mass 28 adheres to the hoof frog portion 30 and hoof sole portion 18, and is held in place thereby. In addition, it is desirable to have the resin mass transparent or at least sufficiently translucent so as to permit viewing the underlying hoof sole portion 18 and frog portion 30. Polyesters, vinyl resins and other resins -meeting the invention criteria can also be used in addition to those listed previously. The term "curing" herein refers to polymerization, whether of the thermosetting or thermoplastic type, between resin precursors, or other processes by which a resin or resins change from a liquid to a solid state, including by loss of a diluent or solvent.

The invention method of treating a horse's hoof for thrush in one embodiment, includes cleaning the hoof bottom wall 19 of debris, depositing onto the wall 19 a wall-adherent, rapidly curing synthetic organic resin composition comprising the resin 28 and dispersed throughout as shown for wall contact a small but effective amount of a thrush medicament 44 comprising a copper salt that does not block the curing of the composition. The resin composition has a viscosity to flow freely to conform to the contours of the hoof bottom wall 19 before curing and cures to a solid mass 29 in situ in the hoof bottom wall volume 22. In treatment of thrush, the cured resin mass 29 is removed after an effective period of treatment, e.g. 4 to 10 days. The adherent properties of the cured resin mass 29 enable the mass to remain in place with the medicament in wall contact continually and therapeutically effective for extended periods.

As noted, in this and the following embodiments, in general, copper sulfate is typically selected as the medicament, particularly a hydrated form of copper sulfate, such as copper sulfate pentahydrate for incorporation as medicament 44 into resin Side B precursor and reagent 36. The medicament is usefully added as a fine powder and at concentration that provide from about 0.5 to 5% by weight in the cured resin mass 39 and dispersed by selecting a two part resin e.g. a urethane resin 28 and incorporating the medicament 44 into one part of the resin for dispersal in the resin composition upon mixing of the two resin parts delivered from cartridges 38, 42 of the dispenser 46. An effective composition 28 is prepared by dispersing about 1-3% by weight of the copper salt medicament 44 in the resin, e.g. by selecting a two part resin (Side A, Side B) as the resin and incorporating the medicament into one part of the resin for dispersal in the resin composition upon mixing of the two resin parts.

The invention method of treating a horse's hoof for thrush, includes cleaning the hoof bottom wall 19 of debris, depositing onto the hoof bottom wall an adherent, rapidly curing urethane resin composition 28 comprising two-part urethane resin precursors 34, 36 and dispersed in at least one part for wall contact a small but effective amount of a thrush medicament 44 suitably powdered or slurried and comprising a copper salt that does not block the curing of the resin composition, i.e. does not limit or restrict unduly the reactions between the precursors or inhibit adequate resin formation. Upon mixing of the precursors 34, 36, the resin composition 28 has a viscosity to flow freely to conform to the contours of the hoof bottom wall 19 before curing. The resin 28 is cured to a solid 29 in situ in the hoof bottom wall volume 22, and thereafter removed after an effective period of treatment.

In this and like embodiments, typically, the method further includes combining the resin two parts 34, 36 from separate cartridges 38, 42 thereof and injecting into the hoof bottom wall volume 22. Volume 22 has, an open mouth 23. The method can includes therefore fixing a web 20 across the volume open mouth 23, and thereafter injecting the synthetic resin parts 34, 36 into the volume 22 under the web and curing and self-adhering the urethane resin composition mass 29 to the hoof bottom wall 19 in moisture excluding relation. The invention provides for maintaining a hygroscopic amount of the copper salt (e.g. medicament 44 as described herein) in the urethane resin composition 28 against moisture inhibition of cure of the in-hoof composition mass 29.

The invention method of treating a horse's hoof 10 for thrush with a moisture reactive urethane resin composition 28 thus includes cleaning the hoof bottom wall 19 of debris, depositing onto the wall an adherent, rapidly curing urethane resin composition 28 comprising two-part urethane resin precursors 34, 36 and dispersing in at least one of these parts for wall contact a small but effective amount of an adjuvant 48, e.g. copper sulfate, comprising a thrush medicament 44 that is hygroscopic against moisture reaction of the urethane resin composition 28 and that does not block the curing of the resin composition upon mixing of the precursors. Resin composition 28 has the viscosity to flow freely to conform to the contours of the hoof bottom wall 19 before curing. The resin composition 28 is then cured to a solid mass 29 in situ in the hoof bottom wall volume 22.

In more detail, the invention method of treating for thrush a horse's hoof 10 having a hoof bottom wall 19 forming an open volume 22, includes combining from a pair of cartridges 38, 42 into a static mixer 43 separate reactive urethane resin components 34, 36, maintaining a thrush medicament 44 in an effective amount in one of the components during the combining of components, forming a rapidly curing urethane resin 28 in an amount suitable for covering the horse hoof bottom wall, conforming the urethane resin to the contours of the hoof bottom wall, curing the urethane resin in situ to mass 29, and later removing the urethane resin mass 29 and medicament 44.

The invention provides a thrush treated horse's hoof comprising a hoof 10 and a hoof bottom wall 19 and a solid synthetic organic resin composition 29, e.g. a urethane resin, containing intimately and uniformly distributed therethrough a small but therapeutically effective amount of an anti-thrush medicament 44 conformed with and adhered to the hoof bottom wall.

The invention thrush treatment product embodiment comprises a thrush treatment for application to horse's hoof 10 having a hoof bottom wall 19, the treatment comprising a synthetic organic resin composition 28 containing distributed therethrough a small but therapeutically effective amount of an anti-thrush medicament 44 to be conformed with and adhered to the hoof bottom wall, optionally in combination with a web 20 fixed to the hoof and adhered to the resin mass 29.

In further detail, the thrush treating product comprises separate components 34, 36 in separate cartridges 38, 42 reactive upon mixing to a synthetic organic resin mass 29, wherein one of the components further comprises a small but effective amount of an anti-thrush medicament 44, and a mixing structure, such as mix tip 43 for uniformly mixing the components and the medicament adjacent a horse hoof bottom wall 19 at a viscosity adapted to substantially conform to and fill the spaces of the bottom wall surface in adhering relation.

The invention thrush treating system has separately packaged resin precursors 34, 36 to be mixed in reactive proportions, and a small but therapeutically effective amount of an anti-thrush medicament 44 that is ineffective to block reaction of the precursors, the medicament being precursor-dispersed in premixed relation.

EXAMPLE 1

A fast-gelling, low hardness gel containing about 1% by weight of a copper sulfate medicament was prepared from a reactive mixture of Part A, Part B urethane resin precursors shown in the TABLE packaged as two equal volumes for dispensing from a dual cartridge dispenser in which dual pistons on a common yoke extrude the separate reactive components through a manifold and into a mix tip comprising a series of baffles arranged to cut and recombine the mixing materials as they progress through the mix tip.

|  | Parts (Wt.) |
|---|---|
| Composition - Side A |  |
| Step 1: |  |
| Methylene-bis-dicyclohexane diisocyanate (Desmodur W) | 31.55 |
| Polyoxy propylene oxide ether polyol, triol (6000 MW) (Multranol 3901) | 45.07 |
| D.B. (Double Boiled) castor oil | 6.48 |
| Step 2: |  |
| Methylene-bis-diphenyl diisocyanate (Isonate 2143L) | 16.9 |
| Total, Part A | 100 |
| Composition - Side B |  |
| Step 1: |  |
| Multranol 3901 | 40.32 |
| Arcol PPG 2025 | 19.2 |

-continued

| | Parts (Wt.) |
|---|---|
| Polyoxy propylene oxide ether polyol, triol (450 MW) (Multranol 4012) | 19.2 |
| Ethylene diamine tetra propoxylate (Quadrol) | 8.64 |
| Butanediol, 1, 4 | 3.84 |
| Step 2: | |
| Tinuvin 765 | 0.48 |
| Tinuvin 213 | 0.48 |
| Bismuth naphthenate (Coscat 83) | 3.84 |
| Step 3: | |
| Cab-O-Sil M5 | 2.00 |
| Cupric Sulfate Pentahydrate | 2.00 |
| Bismuth naphthenate (Coscat 83) | 0.17 |
| Total, Part B | 100.17 |

The Side A precursor components other than Isonate 2413L were mixed together in a suitable vessel, then the Isonate 2413 was mixed in, and the resultant precursor mixture put up in a first chamber of a dual chamber dispenser. Viscosity of the Side A composition was in the range of about 1000-2000 centipoises at about 25.degrees C. The Side B components of Step 1 were mixed together, then the components of Steps 2 and 3 were added and the mixture was put up in the second chamber of the dual chamber dispenser. The Side B viscosity was in the range of about 800-2000 centipoises, also at about 25.degrees C. Generally, but not necessarily, the Side A and Side B compositions are reactive to a urethane polymer when mixed in a 1:1 ratio, as above, making this composition ideal for dispensing from a conventional 1:1 dual chamber cartridge. Other ratios can be used but they are less convenient, and the cartridge dispensers required, e.g. 2:1 are more costly.

A hoof thrush treatment was effected with the composition of EXAMPLE 1 by simultaneously expelling the contents of both chambers of the dual chamber dispenser through the common mix tip where. they were intimately mixed under severe shear conditions into the volume defined by the hoof below the hoof pad. Injection took about 5 seconds. The like viscosities. and the 1:1 mix ratio of the EXAMPLE 1 composition facilitated packaging and dispensing. The sides initially react to a low viscosity in the mix tip and beyond to flow into and fill the hoof bottom wall interstices and then react completely to a solid on the hoof bottom wall within the hoof volume. The low viscosity of the mixed components enables the ready and rapid filling of the small interstices in the hoof wall. The mixture, however, after a working time of about 8 to 12 seconds, gels very rapidly, within about 20 seconds, so that the mixture remains disposed within the hoof volume. The farrier can put the hoof down after this brief gelling time, as the composition is adhered to the hoof wall, and will not drop or squeeze out. The composition is solid and free of voids, cellularity and foam structure, and provides sulfate or other microbial agent or medicament contact with the hoof wall in thrush ameliorating amounts, and effects a cure (removal of thrush) in typically about 4 days, during which the medicament is continually metered to the hoof wall areas affected by thrush. The plug of resin is then removed and replaced with conventional hoof packing. Typical hardness values for the fully gelled composition are in the range of Shore A 40 to 80 after 24 hours at room temperature; incidentally cushioning the hoof although not a foamed composition.

EXAMPLE 2

Example 1 is repeated but using 4 parts by weight of the copper sulfate, while reducing the Multranol content to maintain 100 parts in the composition; thrush reduction is comparable over the four day test period and may be quicker acting.

EXAMPLE 3

Example 1 is repeated but using 10 parts by weight of the copper sulfate (5% by weight of the composition), while reducing the Multranol content to maintain 100 parts in the composition; thrush reduction is comparable over the four day test period and is likely quicker acting than in the previous Examples.

The invention accordingly provides products and methods for improving the health of hoofed animals, particularly horses with a method of treating horse hoof thrush conditions with medicaments held to the affected area by a hoof bottom wall covering material that bodily incorporates the medicament, that depletes the covering material of moisture with a hygroscopic adjuvant that also functions as a medicament, that is delivered as a medicament-modified fluid resin into the affected area from dual cartridges containing separate, reactive precursor components of the material, and the medicament as well, resulting in a thrush-treated horse hoof having a covering material therein that is intimately mixed with particulate medicament typically a sulfate salt that migrates, seeps, blooms or otherwise rises to the interface of the hoof bottom wall and the hoof bottom wall covering in amounts and locations such that the thrush condition is treated without inhibiting adhesion between the hoof covering material and the hoof bottom wall. The invention thrush treatment and product uses a synthetic organic resin matrix and distributed therein a small but therapeutically effective anti-thrush medicament such as a hydrated copper sulfate at about 0.5 to about 5% by weight, the resin matrix, typically a urethane resin, being conformed to the hoof bottom wall in operating proximity to the thrush condition. The thrush treating system has separately packaged resin precursors to be mixed in reactive proportions, and a therapeutic agent that is ineffective to block reaction of the precursors or bonding of the resin product to the hoof bottom wall, the therapeutic agent being precursor dispersed in premixed relation, so as to provide a medicated hoof packing method and product that flows easily and readily into the hoof volume above the hoof bottom wall and the interstices thereof yet sets up nearly immediately to a firm, somewhat resilient mass that adheres to the hoof volume walls against loss of the mass or incursions of debris, all the while treating the hoof host for thrush. The foregoing objects are thus met.

We claim:

1. A method of treating an animal hoof having a thrush condition, including cleaning the hoof bottom wall of debris, depositing onto said hoof bottom wall an adherent, rapidly curing synthetic organic resin composition, said resin composition having dispersed throughout for continuing hoof bottom wall contact an amount of an anti-microbial metal ion donor, said metal ion donor not blocking the curing of said resin composition, said deposited resin composition having a viscosity to flow freely to conform to the contours of said hoof bottom wall, thereafter curing said resin composition to a solid in situ on said hoof bottom wall, the metal ion content of the resin being effective to treat the thrush condition, and removing said cured resin solid after an effective period of treatment.

2. The method according to claim 1, wherein said solid cured resin composition on said hoof bottom wall also provides moisture incursion-proof sealing of said thrush condition during said period of treatment.

3. The method according to claim 1, wherein said antimicrobial is a copper ion donor.

4. The method according to claim 3, wherein a hydrated form of copper sulfate is selected as said copper ion donor.

5. The method according to claim 1, wherein said resin composition is a urethane resin.

6. A method of treating a horse hoof having a thrush condition, including cleaning the hoof bottom wall of debris, depositing onto said hoof bottom wall an adherent, rapidly curing synthetic organic resin composition, said resin composition having dispersed throughout for continuing hoof bottom wall contact an effective amount of-an anti-microbial ion donor that does not block curing of said composition, said deposited resin composition having a viscosity to flow freely to conform to the contours of said hoof bottom wall, thereafter curing said resin composition to a solid in situ on said hoof bottom wall in wall-adhering relation, the amount of anti-microbial ion donor, when dispersed in the organic resin, being effective for the treatment of thrush, and removing said cured resin solid after an effective period of treatment.

7. The method according to claim 6, wherein said solid cured resin composition on said hoof bottom wall provides moisture incursion-proof sealing of said thrush condition during said period of treatment.

8. The method according to claim 6, wherein said metal ion donor is a copper ion donor.

9. The method according to claim 8, wherein the copper ion donor is a hydrated form of copper sulfate.

10. The method according to claim 6, wherein the resin composition is a urethane resin.

11. A method of treating a horse's hoof for thrush, including cleaning the hoof bottom wall of debris, depositing onto said hoof bottom wall an adherent, rapidly curing synthetic organic resin composition, said resin composition having dispersed throughout for wall contact an amount of a thrush medicament comprising a copper salt, the amount of said copper salt being limited so that it does not block curing of said composition, said deposited resin composition having a viscosity to flow freely to conform to the contours of said hoof bottom wall before curing, curing said resin to a solid in situ on said hoof bottom wall, and removing said cured resin after an effective period of treatment, the amount of copper salt in combination with said deposited resin being effective to treat thresh.

12. A method of treating a horse's hoof for thrush, including cleaning the hoof bottom wall of debris, depositing onto said hoof bottom wall an adherent, rapidly curing synthetic organic resin composition, said resin composition having dispersed throughout for wall contact an amount of a thrush medicament comprising a copper salt, said amount of copper salt being effective to treat thrush without blocking curing of said medicament containing resin composition, said deposited resin composition having a viscosity to flow freely to conform to the contours of said hoof bottom wall before curing, curing said resin to a solid in situ on said hoof bottom wall, and removing said cured resin after an effective period of treatment.

13. The method according to claim 12, wherein the copper salt is copper sulfate.

14. The method according to claim 13, wherein the copper salt is a hydrated form of copper sulfate.

15. The method according to claim 14, wherein the copper salt is copper sulfate pentahydrate.

16. The method according to claim 12, wherein the medicament medicant comprises from 0.5 to 5% by weight of copper salt in said resin composition.

17. The method according to claim 12, wherein the medicament comprises about 1-3% by weight of copper salt.

18. The method according to claim 17, wherein said resin is a two part resin and said medicament is incorporated into one part of said resin for dispersal in said resin composition upon mixing of said two resin parts.

19. The method according to claim 12, wherein said resin is a two part resin, said medicament incorporated into one part of said resin for dispersal in said resin composition upon mixing of said two resin parts.

20. The method according to claim 19, wherein the copper salt is copper sulfate pentahydrate.

21. The method according to claim 12, wherein the copper salt is copper sulfate pentahydrate.

22. A method of treating a horse's hoof for thrush, including cleaning the hoof bottom wall of debris, depositing onto said hoof bottom wall an adherent, rapidly curing urethane resin composition comprising Part A and Part B urethane resin precursors, at least one Part having an amount of a copper salt disbursed therein, said copper salt being effective to treat thrush but said amount to not being effective to block said curing of said resin composition upon mixing of said Part A and Part B precursors when dispersed therein, said deposited resin composition having a viscosity to flow freely to conform to the contours of said hoof bottom wall before curing, curing said resin to a solid in situ in said hoof bottom wall with said dispersed copper salt in wall contact, and removing said cured resin and medicament after an effective period of treatment.

23. The method according to claim 22, wherein the copper salt is copper sulfate.

24. The method according to claim 23, wherein the copper salt is a hydrated form of copper sulfate.

25. The method according to claim 24, wherein the copper salt is copper sulfate pentahydrate.

26. The method according to claim 25, wherein about 0.5 to about 5% by weight of said copper salt medicament is dispersed in said resin composition.

27. The method according to claim 26, wherein about 1-3% by weight of said copper salt medicament.

28. The method according to claim 27, wherein said copper medicament is placed into Part B of said resin for dispersal in said resin composition upon mixing of resin Parts A and B.

29. The method according to claim 28, wherein the copper medicant is copper sulfate pentahydrate.

30. The method according to claim 29, wherein said resin Parts A and B from separate cartridges are combined in a single mix tip and the resulting resin composition is deposited onto said hoof bottom wall.

31. The method according to claim 30, also comprising defining an at least partially closed volume over said hoof bottom wall, and depositing said resin composition into said volume against said hoof bottom wall.

32. The method according to claim 31, comprising self-adhering said urethane resin composition to said hoof bottom wall in moisture excluding relation.

33. The method according to claim 32, also comprising maintaining a hygroscopic amount of said copper salt in said urethane resin composition against moisture inhibition of the in situ cure of said composition.

34. The method according to claim 22, comprising combining said resin Parts A and B from separate cartridges in a single mix tip and depositing the resulting resin composition onto said hoof bottom wall.

35. The method according to claim 22, comprising defining an at least partially closed volume over said hoof bottom wall, and depositing said resin composition into said volume against said hoof bottom wall.

36. A method of treating a horse's hoof for thrush with a urethane resin composition that is detrimentally effected by the presence of moisture comprising depositing onto the bottom wall of said hoof a wall-adherent, rapidly curing urethane resin composition comprising two-part urethane resin precursors, at least one part of said two-part precursors having disbursed therein a small but effective amount of an adjuvant that is hygroscopic against moisture reaction of said urethane resin composition and is effective, when disbursed in said resin composition, for treatment of thrush and that does not block curing of said resin composition upon mixing of said precursors, said deposited resin composition having a viscosity to flow freely to conform to the contours of said hoof bottom wall before curing, and curing said resin to a solid in situ on said hoof bottom wall.

37. The method according to claim 36, wherein said adjuvant is copper sulfate.

38. A method of treating a horse's hoof for thrush, said hoof having a hoof bottom wall, comprising feeding from a pair of cartridges each containing different reactive urethane resin precursors, said precursors being fed through a static mixer to combine same, one or both of said resin precursors including a thrush medicament in an effective amount effective to treat thrush without preventing curing of said combined resins, forming a rapidly curing urethane resin from said precursors in an amount suitable for covering said hoof bottom wall, conforming said urethane resin to the contours of said hoof bottom wall, curing said urethane resin in situ, and later removing said urethane resin and medicament.

39. A thrush treatment for application to a horse's hoof having a hoof bottom wall, said treatment comprising a synthetic organic resin composition having distributed there through a therapeutically effective amount of an anti-thrush medicament, said effective amount of anti-thrush medicament not interfering with polymerization of the synthetic organic resin composition so as to form a solid structure conforming to and adhered to said hoof bottom wall.

40. The thrush treatment according to claim 39, in which said medicament comprises copper sulfate present in a small but therapeutically effective amount of from about 0.5 to 5% by weight within said treatment.

41. The thrush treatment according to claim 40, in which said copper sulfate comprises a hydrated form of copper sulfate.

42. The thrush treatment according to claim 41, in which said hydrated copper sulfate comprises copper sulfate pentahydrate present in a small but therapeutically effective amount of from about 1-3% by weight within said treatment.

43. A thrush treating product comprising separate precursors reactive upon mixing to form a synthetic organic resin, one of said precursors comprising an effective amount of an anti-thrush medicament, and a mixing structure for uniformly mixing said precursors and said medicament adjacent a horse hoof bottom wall to a viscosity adapted to substantially conform to and fill the spaces of a bottom wall surface in adhering relation, said resin precursor polymerizing to form a solid resin in the spaces, said amount of the medicament not interfering with the said polymerization.

44. The thrush treating product according to claim 43, in which said anti-thrush medicament comprises copper sulfate.

45. The thrush treating product according to claim 40, in which said copper sulfate comprises a hydrated form of copper sulfate.

46. The thrush treating product according to claim 45, in which said hydrated copper sulfate comprises copper sulfate pentahydrate.

47. The thrush treating product according to claim 46, in which said medicament comprises from 0.5 to 5% by weight of said combined reactive precursors.

48. The thrush treating product according to claim 47, in which said medicament comprises copper sulfate present from about 0.5 to 5% by weight.

49. The thrush treating product according to claim 48, in which said copper sulfate comprises a hydrated form of copper s ulfate.

50. The thrush treating product according to claim 49, in which said hydrated copper sulfate comprises copper sulfate pentahydrate present in an amount of about 1-3% by weight.

51. A thrush treating system having separately packaged resin precursors to be mixed in reactive proportions, and a therapeutically effective amount of a disbursable solid anti-thrush medicament dispersed in one or more of said precursors, said amount ineffective to block a reaction of said precursors.

52. The thrush treating system according to claim 51, in which said anti-thrush medicament comprises copper sulfate.

53. The thrush treating system according to claim 52, in which said copper sulfate comprises a hydrated form of copper sulfate.

54. The thrush treating system according to claim 53, in which said hydrated copper sulfate comprises copper sulfate pentahydrate.

55. The thrush treating system according to claim 51, in which said medicament comprises from 0.5 to 5% by weight of said combined reactive precursors.

56. The thrush treating system according to claim 51, in which said medicament comprises copper sulfate present from about 0.5 to 5% by weight.

57. The thrush treating system according to claim 56, in which said copper sulfate-comprises a hydrated form of copper sulfate.

58. The thrush treating system according to claim 57, in which said hydrated copper sulfate comprises copper sulfate pentahydrate present an amount of about 1-3% by weight.

59. The thrush treating composition comprising the polymerization product of the following and precursors:

| | Parts (Wt.) |
|---|---|
| Precursor A | |
| Methylene-bis-dicyclohexane diisocyanate | 31.55 |
| Polyoxy propylene oxide ether polyol, triol (6000 MW) | 45.07 |
| D.B. (Double Boiled) castor oil | 6.48 |
| Methylene-bis-diphenyl diisocyanate | 16.9 |
| Total, Part A | 100 |
| Precursor B | |
| Polyoxy propyllene oxide ether poly,triol (6000 MW) | 40.32 |
| Polypropylene glycol | 19.2 |
| Polyoxy propylene oxide ether polyol, triol (450 MW) | 19.2 |
| Ethylene diamine tetra propoxylate | 8.64 |
| Butanediol, 1, 4 | 3.84 |
| Hindred amine light stabilizer | 0.48 |
| Benzotriazole UV absorber | 0.48 |
| Bismuth naphthenate | 3.84 |
| Fumed silica | 2.00 |
| Cupric Sulfate Pentahydrate | 2.00 |
| Bismuth naphthenate | 0.17 |
| Total, Part B | 100.17 |

* * * * *

UNITED STATES PATENT AND TRADEMARK OFFICE
CERTIFICATE OF CORRECTION

PATENT NO. : 8,505,162 B2
APPLICATION NO. : 11/720334
DATED : August 13, 2013
INVENTOR(S) : Frederick Pigg et al.

It is certified that error appears in the above-identified patent and that said Letters Patent is hereby corrected as shown below:

In the Claims:

Column 15, Claim 38, Line 24: after "a thrush medicament in an" please delete "effective"

Signed and Sealed this
Nineteenth Day of November, 2013

Teresa Stanek Rea
*Deputy Director of the United States Patent and Trademark Office*